United States Patent

Ulrich

Patent Number: 5,121,506
Date of Patent: Jun. 16, 1992

[54] COLLAPSIBLE VISOR-LIKE HEAD COVERING

[76] Inventor: Jan Ulrich, 1039 S. Parker Rd., F2, Denver, Colo. 80231

[21] Appl. No.: 650,236

[22] Filed: Feb. 4, 1991

[51] Int. Cl.⁵ .................................................. A42B 1/20
[52] U.S. Cl. .................................. 2/177; 2/171.5; 2/195
[58] Field of Search ............... 2/12, 171, 175, 195, 2/196, 209.1, 171.4, 171.5, 171.7, 171.8, 177, 178

[56] References Cited

U.S. PATENT DOCUMENTS

| | | | |
|---|---|---|---|
| 351,466 | 10/1886 | Robbins . | |
| 480,041 | 8/1892 | Schlesinger | 2/175 |
| 971,503 | 9/1910 | Howard . | |
| 1,435,533 | 11/1922 | Knackstedt . | |
| 1,558,142 | 10/1925 | Brenner . | |
| 1,636,889 | 7/1927 | Wittcoff . | |
| 1,666,098 | 4/1928 | Kaul . | |
| 2,007,235 | 7/1935 | Woodside | 2/175 |
| 2,106,571 | 1/1938 | Lipton | 2/171.5 |
| 2,149,468 | 3/1939 | Santise | 2/198 |
| 2,495,041 | 1/1950 | Weiss | 2/177 |
| 2,845,289 | 7/1958 | Cicogna | 287/77 |
| 2,931,046 | 4/1960 | Klein | 2/195 |
| 3,357,026 | 12/1967 | Weigandt | 2/195 |
| 4,096,590 | 6/1978 | Keshock | 2/180 |
| 4,999,851 | 3/1991 | Hall | 2/195 |

FOREIGN PATENT DOCUMENTS

| | | | |
|---|---|---|---|
| 3627 | 7/1900 | Austria . | |
| 968542 | 11/1950 | France | 2/177 |
| 995629 | 12/1951 | France | 2/177 |
| 255391 | 1/1949 | Switzerland | 2/177 |
| 275147 | 7/1951 | Switzerland | 2/177 |
| 666164 | 7/1988 | Switzerland | 2/175 |
| 187553 | 10/1922 | United Kingdom . | |
| 433835 | 8/1935 | United Kingdom | 2/177 |

Primary Examiner—Werner H. Schroeder
Assistant Examiner—Diana L. Biefeld
Attorney, Agent, or Firm—John E. Reilly

[57] ABSTRACT

A collapsible head covering is in the form of a visor-like cap having the usual head-encircling portion, and a visor or bill extends from the head-encircling portion which includes a normally shapeless crescent-shaped section and a wire-like reinforcing member embedded in the outer peripheral edge of the crescent-shaped section so as to cause the visor to assume a generally convex cross-sectional configuration when worn and can be collapsed by twisting the visor into a coiled circular configuration for storage purposes.

16 Claims, 1 Drawing Sheet

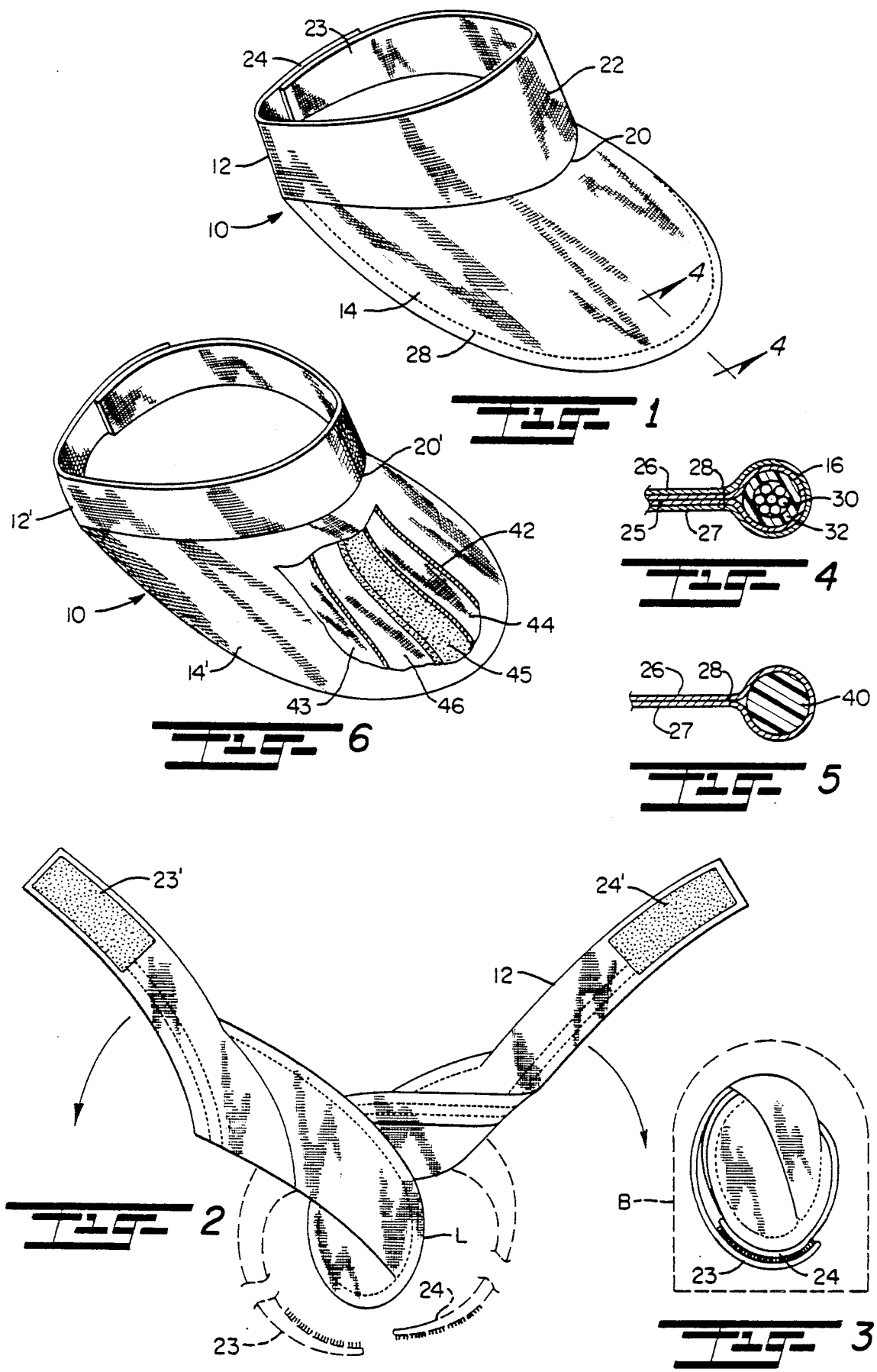

COLLAPSIBLE VISOR-LIKE HEAD COVERING

This invention relates to headwear; and more particularly relates to a novel and improved visor-like cap or hat which can be coiled into a compact condition for convenient storage when not in use.

BACKGROUND AND FIELD OF THE INVENTION

Visor-like caps are in widespread use for various outdoor activities as a sunshade or screen. For instance, they are almost exclusively used by baseball players and by a great number of golfers and tennis players. Typically, the caps are subjected to an extreme amount of abuse, wear and tear as well as being deformed out of their proper configuration when laundered or folded into one's pocket or stuffed into a golf bag pocket. Under repeated use, conventional caps ten to become misshapen and this is especially true of the more popular form of visor in which the entire bill is reinforced with a cardboard or cardboard-like material which when folded or severely bent will not very easily return to its original curved configuration.

It has been proposed in the past to devise full-brimmed hats with outer wire or wire-like reinforcing members which can be coiled into a compact condition for storage purposes and, for example, reference is made to U.S. Pat. No. 2,007,235 to E. R. Woodside and U.S. Pat. No. 2,495,041 to M. Weiss. Similar approaches are disclosed in other U.S. Pat. No. 2,149,468 to J. T. Santise, U.S. Pat. No. 1,636,889 to E. Wittcoff, U.S. Pat. No. 1,558,142 to M. Brenner and U.S. Pat. No. 2,845,289 to E. G. Cicogna, but in most all cases propose the use of some form of special material, such as, a fabric having directional strength or a particular dimensional relationship between the size of the brim and size of the reinforcing member, such as, in the hereinbefore referred to patents to Woodside and Weiss.

Visor-like cap constructions have been devised with deformable reinforcing wires but are typically used in combination with other reinforcing elements and not designed in such a way that the caps can be coiled into a compact storage condition so as not to become misshapen when not in use; yet, when uncoiled, will automatically spring back into their original crescent-shaped configuration with a curved bill when placed on the head of the wearer. Representative patents disclosing visor-like cap constructions with a reinforcing or stiffener section are U.S. Pat. No. 2,931,046 to H. D. Klein, U.S. Pat. No. 1,666,098 to G. P. Kaul, U.S. Pat. No. 971,503 to C. I. Howard, U.S. Pat. No. 351,466 to J. J. Robbins and U.S. Pat. No. 1,435,533 to L. C. Knackstedt. Other foreign patents of interest are British Patent No. 187,553 to W. Schwalbe and Austrian Patent No. 3,627 to J. Komrowsky. A patent of particular interest in this regard is U.S. Pat. No. 3,357,026 to R. C. Wiegandt in which a resilient stay or wire is designed to reinforce and lend a specific shape to the bill of a cap without utilizing a cardboard or similar material in the bill itself. However, in Weigandt, as is true in many of the other visor-like cap constructions, the resilient stay or stiffener member must be removed before the hat can be folded into a collapsed condition for storage.

SUMMARY OF THE INVENTION

Accordingly, it is an object of the present invention to provide for novel and improved headwear and particularly of the visor type which can be efficiently collapsed or coiled into a compact condition for storage when not in use.

It is another object of the present invention to provide for a novel and improved visor-type cap having a wire or wire-like reinforcing member which will establish the shape of the cap when worn and can be coiled with the cap into a compact package when not in use and will automatically return to its original shape or condition when placed on the head of the wearer.

A further object and feature of the present invention is to provide in a head covering for a novel and improved reinforcing member which will serve as the sole means of shaping and support of the head covering and will remain a permanent part of the cap when laundered or folded for storage purposes without becoming misshapen; and further wherein the reinforcing member is so constructed and arranged that its characteristics will not be altered by laundering or cleaning of the cap and is capable of springing back to the desired shape when worn.

A still further object of the present invention is to provide a high strength, resilient reinforcing member for the bill or visor of a cap which can be permanently inserted into the bill, is simple and inexpensive to manufacture and extremely rugged and durable in use.

In accordance with the present invention, a visor-like cap has been devised which is provided with the usual head-engaging or encircling portion, and a visor extending from the head-engaging portion includes an unreinforced, crescent-shaped section, and a wire-like reinforcing member extending around the outer peripheral edge of the crescent-shaped section, the reinforcing member including opposite ends terminating adjacent to said head-engaging portion, the reinforcing member being composed of a wire or wire-like material having a stiffness or straightness such that the visor will assume a generally convex cross-sectional configuration when placed on the head of a wearer and can be twisted into a coiled circular configuration of substantially reduced size in relation to its normal size when worn on the head of a wearer.

In the preferred form, the reinforcing member is comprised of preformed wire rope; i.e., helical strands of wire wrapped into a single cable. Preferably, the rope is encased in an outer flexible plastic sheath. In an alternate form, the reinforcing member is a polyurethane cord either in the form of a solid rod or tubular member having a circular cross-section and of a stiffness corresponding to that of the cable member described. In this relation, when used in combination with a head-encircling portion having free, releasably connectable ends, most desirably the head-encircling portion and the crescent-shaped section are composed of an essentially shapeless material, such as, a soft fabric so that the reinforcing member can be twisted into a tight coil. The free ends of the head-encircling portion are then wrapped several times around the coiled reinforcing member with the free ends reattached to retain the cap in a compact bundle or package which can be easily stored in one's pocket or in a small bag and occupy very little space; yet, when the ends are released, the reinforcing member is sufficiently resilient that it will spring back into its original configuration. A particularly important and favorable characteristic of the reinforcing member is that it exhibits no tendency to kink even when compressed into a tightly coiled condition.

The above and other objects, advantages and features of the present invention will become more readily appreciated and understood from a consideration of the following detailed description of preferred and modified forms of the present invention when taken together with the accompanying drawings in which:

BRIEF DESCRIPTION OF THE DRAWINGS

FIG. 1 is a perspective view of a preferred form of cap in accordance with the present invention;

FIG. 2 is a front view in elevation illustrating the procedure for coiling the preferred form of cap shown in FIG. 1 into a compact storage position;

FIG. 3 illustrates the fully coiled configuration of the cap shown in FIGS. 1 and 2 for stowing in a bag;

FIG. 4 is a cross-sectional view taken about lines 4—4 of FIG. 1;

FIG. 5 is another cross-sectional view of a modified form of reinforcing member incorporated into the bill of a cap; and FIG. 6 is a perspective view of a modified form of cap with portions broken away to illustrate the construction of the bill of the cap.

DETAILED DESCRIPTION OF THE PREFERRED EMBODIMENT

Referring in more detail to the drawings, there is illustrated in FIGS. 1 to 4 a preferred form of invention in the form of a cap 10 which is broadly made up of a head-encircling band 12 and a bill or visor 14 having a wire or wire-like reinforcing member 16 extending around the entire outer peripheral edge of the bill, an inner peripheral edge 20 of the bill being permanently attached to the band 12, such as, by suitable stitching, not shown. The style of cap 10 is given more as a setting for the present invention and is representative of numerous types of visor or cap constructions. For example, the cap may be in the form of a visor having no band 12 but which partially encircles the head, or a cap with a full crown to completely cover the head.

In the preferred form, the head-encircling band 12 is of standard construction comprising one or more layers of a fabric material defining a crown 22 above the visor 14, and opposite sides of the band 12 terminate in free ends 23 and 24 which are releasably attached together as shown. Typically, the free ends are releasably connected to one another by complementary Velcro fastening strips 23' and 24', as shown in FIG. 2, along the facing surfaces of the free ends 23 and 24 so that the ends may be connected to establish the proper fit.

The visor or bill 14 is of generally crescent-shaped configuration and is suitably made up of upper and lower fabric layers 26 and 27, respectively, and an intermediate layer of cotton batting or muslin 25 or other flexible or soft fabric material; and the layers 25–27, as shown in FIG. 4, are doubled over the reinforcing member 16 and seamed together as at 28 to closely surround and securely retain the reinforcing member 16 in position. An important feature of the present invention resides in the ability of the reinforcing member 16, by virtue of its composition and characteristics, to operate as the exclusive means of support and shaping of the bill when worn so as to be of generally upwardly convex configuration in a direction circumferentially across the inner peripheral edge 20, and the degree of convexity is progressively reduced in a radially outward direction toward the outer peripheral edge of the bill.

Again, in the preferred form, the reinforcing member 16 traverses the entire extent of the outer peripheral edge of the bill 14 and is preferably comprised of a preformed wire rope or helical strands of wire 30, and the strands are wrapped together and encased within a plastic sheath 32. A reinforcing member which lends itself particularly well for use in this application is that referred to as tiller cable and which is made up of galvanized or stainless steel wire strands coated with a vinyl or other plastic material. In the form shown, a 7×7 3/32" galvanized steel wire is coated with vinyl to 3/16", such as, Part No. 51820 manufactured and sold by Tie Down Engineering of Atlanta, Ga. The wire strands are wrapped or twisted together in the form of a helix which when encased within a vinyl sheath as at 32 possesses sufficient resiliency that it will bend into the generally crescent-shaped or arcuate configuration as illustrated in FIG. 1 when the cap 10 is placed in an encircling position around the head of the wearer. By forming the strands together into a single helix 30, the member 16 will not bend as easily as a single strand and will effectively resist any tendency to kink or crease when folded or coiled.

The inner peripheral edge of the bill 14 when secured to the band 12 will lend additional support or reinforcement to the cap when placed on the head, but the major reinforcement and support is provided by the member 16 and to the extent that the crescent-shaped layers 25, 26 and 27 require no other shaping or supporting means, such as, cardboard, plastic or the like customarily used in conventional visor or cap constructions. In this relation, the reinforcing member, being constrained to follow the curved outline of the outer peripheral edge of the bill possesses a sufficient degree of straightness or memory, that it will exert a slight degree of tension on the fabric material of the bill so as to maintain it in a taut or stretched condition.

As further illustrated in FIGS. 2 and 3, the shapeless characteristics of the bill 14 when combined with the limited resiliency of the reinforcing member 16 permit convenient folding or collapsing of the cap 10 into a compact package when not in use. Thus, by disengaging the free ends 23 and 24, the brim or outer peripheral edge of the bill 14 is twisted into a small loop or coil as designated at L. The free ends 23 and 24 of the band 12 are then wrapped around the loop L, as shown in FIG. 2, with the free end 23 facing in and the free end 24 facing out so that upon completion of wrapping can be secured together. This wrapping may take place or be done in a single plane in surrounding relation to the loop or by wrapping over and under the loop while maintaining the loop in a tightly coiled condition. For instance, the free end 24 as shown in FIG. 2 would be wrapped in a clockwise direction around the loop, followed by wrapping the end 23 in an opposite direction, counterclockwise around the loop L and the partially wrapped free end 23 until the free end 24 moves into mating engagement with the end 23, essentially as shown in the completed condition in FIG. 3. FIG. 3 also illustrates a typical manner of storage of the cap by inserting the wrapped cap into a small bag or pouch B.

In the modified form shown in FIG. 6, like parts are correspondingly enumerated with prime numerals to those of FIGS. 1 to 4 and comprises a cap 10' having a band 12' and visor or bill 14'. As before, the inner peripheral edge 20' of the visor is permanently attached to the band 12'; however, the visor portion 14' consists of an upper fabric layer 42 and a lower fabric layer 43 separated by intermediate layers consisting of equal thicknesses of a heavyweight interfacing layer 44, layer of cotton batting or muslin 45 and another heavyweight interfacing layer 46.

A reinforcing member 40, as shown in FIG. 5, extends continuously around the outer peripheral edge between opposite sides of the bill 14' at their points of attachment to the band 12'. The modified form of reinforcing member 40 has characteristics comparable to those of the reinforcing member 16 as described but is composed of an extruded plastic cord and preferably composed of a polyurethane material. When the cord is in the form of a solid rod, the durometer or hardness would be in the range of 50 to 60 shore and when of tubular configuration would be more in the range of 80 to 90 shore. The diameter of the cord is typically in the range of ⅛" to 3/16", and the same would be true of a tubular cord member. Either type of cord has sufficient resiliency or straightness that when inserted into the outer curved peripheral edge of the bill 14 will be under a certain amount of tension tending to stretch the layers of material 42 to 46 so as to be taut and assume a generally convex configuration as previously described in the preferred form of FIGS. 1 to 4. The tension in the cord 40 is further increased by twisting or coiling into the storage position as described with reference to the preferred form of reinforcing member 16 in FIGS. 2 and 3.

From the foregoing, it will be appreciated that a novel and improved cap has been devised in which the sole means of reinforcement of the brim or visor is a wire or wire-like reinforcing member which will also serve to shape the visor when worn but nevertheless can remain a permanent part of the cap when laundered or folded for storage purposes without becoming misshapen. A wire cable, such as, the reinforcing member 16 has been found to be particularly effective by virtue of its combined resilience and stiffness for a given cross-sectional thickness. Here it is important that the cross-sectional thickness at least approximates the thickness of the bill 14 or 14', as the case may be, so that it can be twisted into a tight coil without kinking or permanently bending. Moreover, when the cap is to be worn, the reinforcing member should have sufficient resilience that it will immediately spring back into its original configuration. In the modified form of invention shown in FIGS. 5 and 6, a plastic reinforcing member 40 is illustrated and which will demonstrate the same ability to be coiled into a compact condition. However, by virtue of the increased number of layers making up the bill 14', the cap cannot be as tightly coiled as in the preferred form of FIGS. 1 to 4. It will be evident in this respect that the reinforcing members 16 and 40 are interchangeable for used in different types and styles of caps.

It is therefore to be understood that various other modifications and changes may be made in the construction and arrangement of elements comprising the preferred and modified forms of invention as well as the composition of materials utilized without departing from the spirit and scope of the present invention as defined by appended claims and reasonable equivalents thereof.

I claim:

1. In a head covering, a visor-like cap provided with a flexible head-encircling portion, the improvement comprising:

a visor extending from said head-encircling portion including an unreinforced, flexible crescent-shaped section, and an elongated reinforcing member embedded in an outer peripheral edge of said crescent-shaped section, said reinforcing member including opposite ends terminating adjacent to said head-encircling portion, said reinforcing member composed of a wire or wire-like material having a bias and tendency to straighten itself such that said visor will assume a generally convex configuration when placed on the head of a wearer and when not worn said visor including said reinforcing member can be twisted into a tightly coiled, loop-shaped configuration of substantially reduced size in relation to its normal size when worn on the head of a wearer.

2. In a head covering according to claim 1, said visor being characterized by being manually twisted without kinking into a circular coil with said reinforcing member coiled through greater than 360° into a coiled portion with said opposite ends of said reinforcing member overlapping said coiled portion.

3. In a head covering according to claim 1, said head-encircling portion having free, releasably connectable ends which when said visor is twisted into a coil are wrapped around said coil.

4. In a head covering according to claim 1, said reinforcing member comprised of helical strands of wire and a flexible sheath encircling said wire.

5. In a head covering according to claim 4, said wire being a galvanized steel wire.

6. In a head covering according to claim 1, said reinforcing member being in the form of a plastic cord having a circular cross-section.

7. In a head covering according to claim 6, said cord being in the form of a solid rod having a durometer in the range of 50 to 60 shore.

8. In a head covering according to claim 6, said cord being in the form of tubing having a durometer in the range of 80 to 90 shore.

9. In a head covering wherein a cap is provided with a flexible head-encircling portion, the improvement comprising:

a visor extending from said head-encircling portion including an unreinforced crescent-shaped section composed of a shapeless material, such as, a soft fabric, and reinforcing means in the form of an elongated stiffener member embedded in an outer peripheral edge of said crescent-shaped section and traversing the length thereof, said stiffener member including opposite ends terminating adjacent to said head-encircling portion, said crescent-shaped section surrounding said stiffener at its outer peripheral edge, said stiffener member composed of a resilient wire or wire-like material having a tendency to straighten itself such that said reinforcing means will cause said visor to be stretched into an upwardly convex configuration when placed on the head of a wearer and when not worn said visor including said reinforcing member can be twisted into a tightly coiled circular or loop-shaped configuration of substantially reduced size in relation to its normal size when worn on the head of a wearer.

10. In a head covering according to claim 9, said head-encircling portion having free, releasably connectable ends which when said visor is twisted into a coil are wrapped in circular fashion in overlapping relation to one another and in surrounding relation to said visor.

11. In a head covering according to claim 10, said visor having upper and lower layers of a soft fabric material, said stiffener interposed between said upper and lower layers, and a seam joining said upper and lower layers together in closely surrounding relation to said stiffener along said outer peripheral edge of said visor.

12. In a head covering according to claim 9, said stiffener member composed of a tiller cable having strands of wire and a flexible sheath encircling said strands.

13. In a head covering according to claim 12, said wire being a preformed wire rope.

14. In a head covering according to claim 9, said stiffener member being in the form of a polyurethane cord having a circular cross-section in the range of ⅛" to 3/16" in diameter.

15. In a head covering according to claim 9, said stiffener member being in the form of a solid resilient rod having a durometer in the range of 50 to 60 shore.

16. In a head covering according to claim 9, said stiffener member being in the form of tubing having a durometer in the range of 80 to 90 shore.

* * * * *